United States Patent [19]

Yang et al.

[11] 4,433,196
[45] Feb. 21, 1984

[54] COLOR PRECURSOR REMOVAL FROM DETERGENT RANGE ALKYL BENZENES

[75] Inventors: Kang Yang; James D. Reedy, both of Ponca City, Okla.

[73] Assignee: Conoco Inc., Ponca City, Okla.

[21] Appl. No.: 392,431

[22] Filed: Jun. 25, 1982

[51] Int. Cl.³ .............................................. B01D 15/00
[52] U.S. Cl. .................................... 585/823; 210/690; 210/917
[58] Field of Search ....................... 210/679, 690, 917; 585/820, 823, 829; 252/436, 439, 455 Z, 461, 472

[56] References Cited

U.S. PATENT DOCUMENTS

| | | | |
|---|---|---|---|
| 2,688,633 | 9/1954 | Cohen | 585/823 |
| 3,306,945 | 2/1967 | Conviser | 585/823 |
| 3,338,983 | 8/1967 | Thompson | 585/823 |
| 3,719,704 | 3/1973 | Marquis | 585/823 |

Primary Examiner—Ivars C. Cintins
Attorney, Agent, or Firm—Robin M. Davis

[57] ABSTRACT

Extremely effective adsorbants are provided for removing color precursors from detergent range alkyl benzenes prior to sulfonation. The adsorbers provided are specific crystalline zeolites in a silica alumina matrix and bauxite clay having at least one material selected from the group consisting of ferric oxide, titanium dioxide and zirconium oxide which is activated by sulfuric acid then calcined to provide the effective adsorbant.

10 Claims, No Drawings

COLOR PRECURSOR REMOVAL FROM DETERGENT RANGE ALKYL BENZENES

The present invention relates to the production of detergent range alkyl benzenes which are substantially free of color precursors causing color after such materials are sulfonated. More specifically, the present invention provides for a method of removing color precursors from detergent range alkyl benzenes prior to sulfonation by contacting such alkyl benzenes with an adsorbant in order to remove color precursors.

The alkylation of aromatic hydrocarbons, in particular benzene, with olefins or alkyl chlorides to produce the corresponding alkyl aromatics by using aluminum chloride as an alkylation catalyst has long been practiced as a step in the manufacture of alkyl aryl sulfonate detergents. Another method of producing such alkylated aromatic hydrocarbons is through the use of hydrofluoric acid. However obtained, the alkylated aromatic hydrocarbons, generally alkyl benzene, are subsequently sulfonated and neutralized to give the desired salt of the alkyl aryl sulfonic acid, which constitutes the active detergent material. The prior art recognizes that the crude mixture of unreacted components, alkylated aromatics, high molecular weight compounds, catalysts, and hydrogen chloride called alkylate (obtained from the alkylation process) requires purification if high quality detergents are to be produced and certain processing problems are to be avoided. Among such processing problems are the fouling of heat exchangers, reboilers and the like. For example, in the distillation of crude alkylates severe fouling of heat exchange equipment, particularly preheaters and reboilers occurs, resulting in the need for frequent down time to remove such fouling.

The prior art also recognizes that the sulfonation of alkyl aryl hydrocarbons has generally followed a procedure wherein sulfuric acid or oleum is used to sulfonate the alkyl aryl hydrocarbon. Other sulfonating agents have been used. Whatever sulfonating agent is used, the resulting sulfonic acid yields a dark colored sulfonate when neutralized with a base such as sodium hydroxide. These dark colored sulfonates are useful in only a relatively few applications. Therefore, various methods have been suggested for removing such color bodies which, impart color to the sulfonate. These methods have involved treating the sulfonate with bleaching agents such as peroxide or acidic reagents such as sulfuric or hydrochloric acid. Other methods have involved blowing the aqueous sulfonate solution with oxidizing gas, such as free oxygen.

Representative but non-exhaustive examples of such art include U.S. Pat. No. 2,932,677 directed to the method of removing color precursors from alkyl aryl hydrocarbons by treating dodecyl benzene with sulfuric acid followed by clay treating. A comparative example (Example 5) shows that this treatment does not provide a substantial improvement over untreated dodecyl benzene. U.S. Pat. No. 3,835,037 teaches the treatment of an aromatic fraction with a clay having acidic cites. U.S. Pat. Nos. 2,778,863 and 2,775,632 teach treating aromatic hydrocarbons with clay.

However, none of these methods have been entirely satisfactory because of the expenditure of materials, and time. In addition the products obtained from such treatments have not been improved greatly in color. In many cases the resulting improvement has been only temporary.

It would therefore be of great benefit to provide a simple method and process for removing color from sulfonated alkyl aryl hydrocarbons.

It is therefore an object of the present invention to provide a method for removing color precursors from alkyl aryl hydrocarbons. Other methods will become apparent to those skilled in this art as the description proceeds.

We have now discovered a method and specific adsorbants capable of removing color precursors from alkyl aryl hydrocarbons prior to sulfonation. Specifically, our method comprises contacting alkyl benzene prior to sulfonation with a solid adsorbant to remove color precursors, wherein said adsorbant is at least one material selected from the group consisting of bauxite clays containing at least one component selected from the group consisting of ferric oxide, titanium dioxide, and zirconium oxides, mixing said clay with sulfuric acid, and then calcining the mixture at a temperature and time sufficient to activate the adsorbant, and a crystalline zeolite suspended in a silica alumina matrix, wherein said adsorbant contains from about 5% to about 20% by weight of zeolite based on the total weight of the adsorbant.

The adsorbants of the present invention remove certain polyaromatic impurities which cause color in sulfonated alkyl benzene. These precursors are removed in a fixed bed process using sulfuric acid-treated and subsequently calcined clay or zeolite in the silica alumina matrix. Combinations of these materials can be used. These materials are most effective for detergent range alkyl benzenes containing high 2-phenyl isomer content (generally above about 20% by weight) which are currently manufactured by the aluminum chloride alkylation of benzene with alkyl chloride. The resulting feedstock contains some polyaromatic impurities which cause color problems in the subsequent sulfonation step. Current commercial processes to remove these color precursors are carried out by a succession of four processing steps. Initially, the materials are washed with concentrated sulfuric acid, neutralized with aqueous sodium hydroxide, then dried over solid sodium hydroxide flake and finally passed through a clay bed adsorption to remove any carryover. This process requires high consumption of reagents and provides extremely difficult disposal problems associated with waste streams. Finally, this process has high maintenance costs due to the highly corrosive materials used.

In contrast, the present invention avoids all these difficulties by simply treating the alkyl aromatic benzene prior to sulfonation to remove precursors which, upon sulfonation, cause the color difficulty.

The concentration of the color precursors in alkyl benzenes is determined spectrophotometrically as absorbance at 368 nanometers (nm) wavelength. It has been determined that surfactants with acceptable color are produced when the absorbance of the alkyl benzenes in this wavelength is less than 0.06. Generally, the absorbance of an untreated alkyl benzene feed produced from an aluminum chloride catalyzed process is about 0.44.

Of the adsorbants of the present invention, the zeolites suspended in a crystalline synthetic silica alumina is preferred. However, both adsorbants described herein provide extremely effective removal of color precursors for sulfonated alkyl benzene when used to remove such color precursors prior to the sulfonation itself.

The clay adsorber of the present invention is a bauxite clay containing at least one material selected from the group consisting of ferric oxide, titanium dioxide and zirconium oxide. This clay is activated for effective precursor adsorbancy by mixing with sulfuric acid and then calcining the mixture at a temperature and time sufficient to activate the adsorbant prior to use.

Normally the adsorbant will contain from about 0.1 to about 20% by weight based on the total weight of the bauxite clay of ferric oxide and from about 0.1 to about 20% by weight titanium dioxide and from 0.1 to 20% by weight zirconium oxide based on the total weight of the clay. Within these ranges the clay is found to be an effective adsorbant. However, it is preferred that the clay contain from about 0.2 to about 12% by weight of these materials.

The bauxite clay so described is then mixed with sulfuric acid. The sulfuric acid used can be either concentrated or diluted, but the clay must contact from about 0.1 to about 20% by weight of sulfuric acid for effective color removal. It is preferred that from about 0.5 to about 15% by weight of sulfuric acid be used.

After mixing the sulfuric acid with the bauxite clay, the mixture is calcined at a temperature and time sufficient to activate the adsorbant for color precursor removal. Time and temperature of this activation will vary considerably, but normally the calcination is carried out at a temperature of from about 300° C. to about 700° C. However, temperatures of from about 500° to about 600° C. are preferred. The time at this temperature is simply a time sufficient to make the catalyst efficient in removing the color precursors. This time can vary widely and is not critical other than being sufficient for activation to occur.

The bauxite clays useful in the practice of the present invention are found naturally occurring in nature. Many clays with the composition described can be utilized. Representative but non-exhaustive examples of bauxite clays useful in the present invention are Millwhit percolation grade (10-30 mesh) bauxite clays (trademark of and sold by The Milwhit Co. Inc., Houston, Tex.).

A more preferred adsorbant is a crystalline synthetic alumina often used as a cracking catalyst. In this adsorbant, minute crystal zeolites (from about 5 to about 20 weight percent, preferably from about 6 to about 12 weight percent by weight) are suspended in a silica-alumina matrix. The silica-alumina matrix contains from about 10 to about 30 weight percent alumina.

Representative examples of suitable zeolite adsorbants are AGZ cracking catalysts such as AGZ 50, AGZ 200, and AGZ 290, (trademark of and sold by Davidson Chemical Company, a division of Grace), Aerocat 5-4, Aerocat TS-150, TS-170 and T8-260 (trademark of and sold by American Cyanamid Co.) and Filtrol Company's Grade 800 and Grade 810 crystalline synthetic silica-alumina.

When utilizing the adsorbants of the present invention in removing color precursors from alkyl benzenes prior to sulfonation, the alkyl benzene is simply contacted with the adsorbant for a time sufficient to remove the precursor. This time can vary widely depending upon the amount of precursor in the alkyl benzene.

The present invention is best utilized by passing the alkyl benzene through the adsorbant at a liquid hourly space velocity (LHSV) of from about 0.1 to about 10. However, an LSHV of from about 0.5 to about 5.0 is preferred and an LHSV of from 1 to 4 is most preferred.

The adsorbance of the color precursor is carried out at any convenient temperature and normally room temperature is satisfactory.

Pressure or lack of pressure is not detrimental to the present invention and the adsorbance can be carried out at any pressure convenient, whether above or below ambient. Tests were carried out at atmospheric pressure.

The invention is more concretely described with reference to the examples below wherein all parts and percentages are by weight unless otherwise specified. The examples are provided to illustrate the present invention and not to limit it.

The adsorbants of the present invention were prepared and compared to commonly known adsorbants such as silica-alumina, rare earth exchange zeolite, silica gel, acid treated alumina, ion exchange resins, and the hydrogen form of zeolite.

EXAMPLE 1

A bauxite clay adsorbant of the present invention was prepared by sulfuric acid impregnation of clay and subsequent calcination. The clay used was Milwhit percolation grade bauxite (trademark of and sold by The Milwhit Co. Inc., 10/30 mesh) having from 75 to 78 weight percent alumina, from 8 to 16 weight percent ferric oxide, from 7 to 9 weight percent silica, 4 weight percent titanium dioxide, and from 6 to 7 weight percent volatile matter. A mixture of 100 grams of this clay with 20 grams of concentrated sulfuric acid was prepared. The mixture was evaporated to dryness on a rotary evaporator and calcined in atmospheric air at 550° C. for 15 hours. The resulting adsorbant was introduced into a ½ inch stainless steel tube having a 12 cubic centimeter (cc) volume and an adsorbancy run was made at room temperature and an LHSV of 2.5.

The alkyl benzene feed used was produced by alkylating from 10 to 14 carbon atoms linear alkylcholorides with benzene using an aluminum chloride catalyst. The concentration of the color precursor was determined using a spectrophotometer as absorbance at 368 nanometers wavelength. After adsorbance over the bauxite clay, samples of the treated alkyl benzene feed were again checked at 368 nanometers for absorbance. The results are set forth in Table 1 below.

TABLE 1

| Acid-activated bauxite clay | |
|---|---|
| Time, (Hr) | Absorbance |
| 0–1 | 0.024 |
| 1–2 | 0.041 |
| 2–3 | 0.053 |
| 3–4 | 0.061 |

Thus the capacity of the adsorbant was seen to be 10 volumes of alkyl benzene per volume of adsorbant.

EXAMPLE 2

A comparison of other adsorbants was carried out utilizing the same alkyl benzene feed wherein the procedure was exactly as described in Example 1. The silica alumina adsorbant, the rare earth exchange zeolite adsorbant and the H form of zeolite adsorbant were all activated prior to use at 550° C. for 15 hours. Silica gel was activated prior to use at 170° C. for 15 hours. The sulfuric acid treated alumina was impregnated with 20% acid and then calcined at 550° C. for 15 hours prior to use. The results of these adsorbancy tests as determined at 368 nanometers wavelength were determined. It was apparent that none of these materials were effective in reducing the color precursors to an acceptable level. The results are set forth in Table 2.

TABLE 2

| Adsorbent (12 cc) | Absorbence (First 30 cc of the Product) |
|---|---|
| Silica alumina | 0.170 |
| Rare earth exchanged zeolite | 0.250 |
| Silica gel | 0.284 |
| $H_2SO_4$—treated alumina | 0.089 |
| Ion exchange resin (H—form, dried) | 0.250 |
| H—form of zeolite | 0.107 |

EXAMPLE 3

A crystalline synthetic silica alumina used as a cracking catalyst (zeolite AGZ-50, trademark of and sold by Davidson Chemical Company, a subsidiary of Grace) was utilized as an absorbant. 12 cubic centimeters (cc) of this catalyst were utilized in treating the same alkyl benzene feed as described in Examples 1 and 2 under the same conditions. Absorbance in the range of the color precursors were extremely low. At an LHSV of 2.5, the zeolite containing adsorbant was about 100 percent effective in removing color precursors.

The crystalline synthetic silica-alumina adsorbant was compared directly with the acid treated, calcined bauxite clay adsorbant of Example 1. The results are set forth in Table 3.

TABLE 3

Comparison of Zeolite-Containing Cracking Catalyst and $H_2SO_4$—Treated Clay

| Time, (Hr) | Absorbence (%) Example 3 | Absorbence (%) Example 1 |
|---|---|---|
| 0-1 | 0.003 | 0.024 |
| 1-2 | 0.002 | 0.041 |
| 2-3 | 0.004 | 0.053 |
| 3-4 | 0.008 | 0.061 |
| 4-5 | 0.027 | — |
| 5-6 | 0.047 | — |

The data clearly shows that the adsorbants of the present invention are many times more effective in removing color precursors from detergent range alkyl benzene prior to sulfonation than the adsorbants of the prior art. The most preferred adsorbant is the zeolite containing cracking catalyst.

The present invention thus provides novel adsorbants useful in the removal of color precursors from alkyl benzene prior to sulfonation. The adsorbants and method circumvent the material intensive, time intensive and maintenance intensive processes of the prior art, while providing a much more effective color precursor removal.

While certain embodiments and details have been shown for the purpose of illustrating this invention, it will be apparent to those skilled in this art that various changes and modifications may be made herein without departing from the spirit or scope of the invention.

We claim:

1. A method for removing precursors causing color in sulfonated alkyl benzene from said alkyl benzene prior to sulfonation comprising contacting non-sulfonated alkyl benzenes with a solid adsorbent to remove said precursors, where said adsorbent is at least one material selected from the group consisting of (1) bauxite clays containing from about 0.1 to about 20% by weight of at least one material selected from the group consisting of ferric oxide, titanium dioxide, and zirconium oxide, said clay contacted with from about 0.1 to about 20% by weight of sulfuric acid, then activated for removal of color precursors by calcining the mixture at a temperature and time sufficient to activate the adsorbent prior to use, and (2) crystalline zeolites suspended in a silica alumina matrix, wherein said adsorbent contains from about 5% to about 20% by weight of zeolite, based on the total weight of the adsorbent, and then activated for removal of color precursors by calcining the mixture at a temperature and time sufficient to activate the adsorbent prior to use.

2. A method as described in claim 1 wherein the adsorbent is bauxite clay.

3. A method as described in claim 2 wherein the alkyl benzene is contacted with the adsorbent for a time sufficient to remove the color precursors.

4. A method as described in claim 2 wherein the alkyl benzene is placed through the adsorbent at a liquid hourly space velocity of from about 0.1 to about 10.0.

5. A method as described in claim 4 wherein the calcination of the adsorbent is carried out at a temperature of from about 300° C. to about 700° C.

6. A method as described in claim 5 wherein the bauxite clay contains from about 0.5 to about 10% by weight iron oxide, from about 0.5 to about 10% by weight of titanium dioxide and from about 0.5 to 10% zirconium oxide based on the total weight of the bauxite.

7. A method as described in claim 1 wherein the adsorbent is a crystalline zeolite suspended in a silica alumina matrix.

8. A method as described in claim 7 wherein the silica alumina matrix contains from about 10 to about 30 weight percent alumina based on the total adsorbent weight.

9. A method as described in claim 8 wherein the alkyl benzene is contacted with the adsorbent for a time sufficient to remove color precursors.

10. A method as described in claim 9 wherein the alkyl benzene is passed through the adsorbent at a liquid hourly space velocity of from about 0.1 to about 10.0.

* * * * *